(12) United States Patent
Tumey

(10) Patent No.: US 7,346,390 B1
(45) Date of Patent: Mar. 18, 2008

(54) APPETITE SUPPRESSION DEVICE

(76) Inventor: Davis M. Tumey, 5018 Newcastle La., San Antonio, TX (US) 78249

( * ) Notice: Subject to any disclaimer, the term of this patent is extended or adjusted under 35 U.S.C. 154(b) by 417 days.

(21) Appl. No.: 10/068,049

(22) Filed: Jan. 4, 2002

Related U.S. Application Data

(63) Continuation-in-part of application No. 09/933,030, filed on Aug. 20, 2001, now Pat. No. 6,678,557.

(51) Int. Cl.
*A61N 1/00* (2006.01)

(52) U.S. Cl. .......................................................... 607/2

(58) Field of Classification Search ............ 607/1–156, 607/2, 72–76
See application file for complete search history.

(56) References Cited

U.S. PATENT DOCUMENTS

| | | | | |
|---|---|---|---|---|
| 4,503,863 A | * | 3/1985 | Katims | |
| 4,646,744 A | * | 3/1987 | Capel | |
| 5,190,035 A | * | 3/1993 | Salo et al. | |
| 5,735,143 A | * | 4/1998 | Tanaka | |
| 5,913,836 A | * | 6/1999 | Groux | 601/21 |

* cited by examiner

*Primary Examiner*—Scott M. Getzow
(74) *Attorney, Agent, or Firm*—Wayne J. Colton, Inc.

(57) ABSTRACT

An electro-acupuncture based appetite suppression device comprises a headset, having integrated therein a plurality of electrodes, for delivering to the tragus region of a user a mild electrical stimulus generated within a portable controller. The headset is in electrical communication with the controller through a conventional flexible cord provided with a plug. The controller comprises output circuits for delivering a 24 volt output and either a waveform generating circuit or a waveform conditioning circuit or both.

34 Claims, 4 Drawing Sheets

APPETITE SUPPRESSION DEVICE

RELATED APPLICATION

The present application is a continuation-in-part of U.S. patent application Ser. No. 09/933,030 filed Aug. 20, 2001 now U.S. Pat. No. 6,678,557. By this reference, the full disclosure of U.S. patent application Ser. No. 09/933,030 is incorporated herein as though now set forth in its entirety.

FIELD OF THE INVENTION

The present invention relates to methods and apparatus for weight control. More particularly, the invention relates to a device for use in providing an electro-acupuncture signal to the tragus regions of a human, thereby assisting the human in resisting the urge to consume food products.

BACKGROUND OF THE INVENTION

The tragus regions of humans are known locations for the application of both acupressure and acupuncture therapy in control of appetite. Unfortunately, while some individuals may have varied success in the self-application of acupressure therapy, almost none are able to self-administer acupuncture therapy. Additionally, neither therapy may be readily applied during activities such as running or walking, both of which are good activities for those attempting weight loss.

It is therefore an overriding object of the present invention to provide a small, lightweight and portable device for the provision of an electrical signal adapted to stimulate the tragus region of a human user, thereby assisting the user in the avoidance of food products. It is a further object of the present invention to provide such a device as may be utilized in virtually any environment and during virtually any activity.

SUMMARY OF THE INVENTION

In accordance with the foregoing objects, the present invention—an electro-acupuncture based appetite suppression device—generally comprises a headset, having integrated therein a plurality of electrodes, for delivering to the tragus region of a user a mild electrical stimulus generated within a portable controller. The headset is preferably in electrical communication with the controller through a conventional flexible cord provided with a plug, allowing the controller to be worn by the user on a belt clip (especially desirable during activities such as walking or jogging) or simply carried in hand or placed on a nearby table or the like. The controller comprises output circuits for delivering a 24 volt output and either a waveform generating circuit or a waveform conditioning circuit or both.

Finally, many other features, objects and advantages of the present invention will be apparent to those of ordinary skill in the relevant arts, especially in light of the foregoing discussions and the following drawings, exemplary detailed description and appended claims.

BRIEF DESCRIPTION OF THE DRAWINGS

Although the scope of the present invention is much broader than any particular embodiment, a detailed description of the preferred embodiment follows together with illustrative figures, wherein like reference numerals refer to like components, and wherein.

DETAILED DESCRIPTION OF THE PREFERRED EMBODIMENT

Although those of ordinary skill in the art will readily recognize many alternative embodiments, especially in light of the illustrations provided herein, this detailed description is exemplary of the preferred embodiment of the present invention, the scope of which is limited only by the claims appended hereto.

Figure 1:
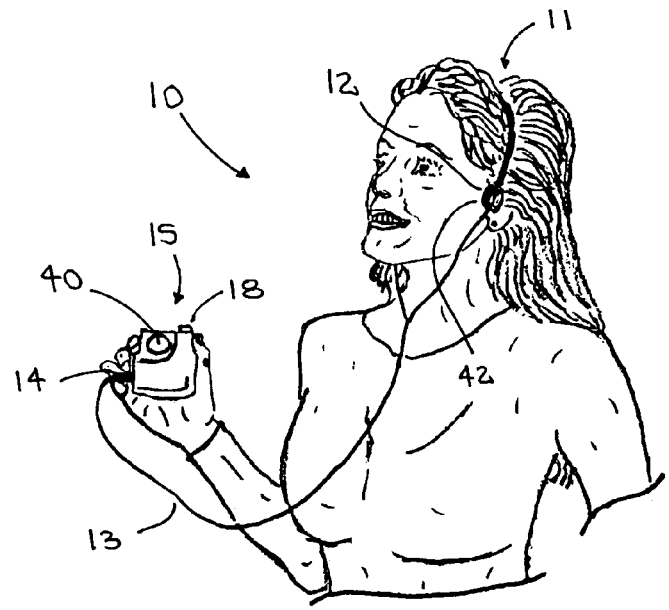
FIG. 1 shows, in a perspective view, the preferred embodiment of the appetite suppression device of the present invention as used in operation.

Referring now to FIG. 1, the appetite suppression device 10 of the present invention is shown to generally comprise a headset 11, having integrated therein a plurality of electrodes 12, for delivering to the tragus region 42 of the user a mild electrical stimulus generated within a portable controller 15. As shown in the figure, the headset 11 is preferably in electrical communication with the controller 15 through a conventional flexible cord 13 provided with a plug 14. In this manner, the controller 15 may be worn by the user on a belt clip (especially desirable during activities such as walking or jogging) or may be simply carried in hand or placed on a nearby table or the like.

Figure 2:
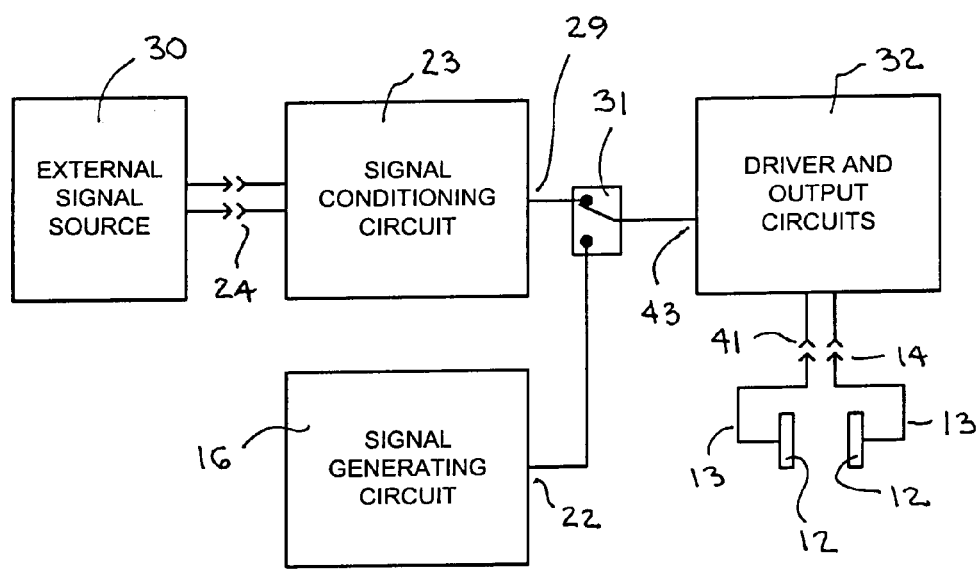
FIG. 2 shows, in a functional block diagram, the various components of the appetite suppression device of FIG. 1.

As shown in FIG. 2, the controller 15 generally comprises a signal generating circuit 16 and/or a signal conditioning circuit 23 having their respective outputs 22, 29 in communication with the input 43 to driver and output circuits 32. As will be better understood further herein, the present invention may be practiced with either the signal generating circuit 16 or the signal conditioning circuit 23. In embodiments comprising both, however, a mode selection switch 31 is also preferably provided to select which output 22, 29 is to be in communication with the input 43 to the driver and output circuits 32.

Figure 3:
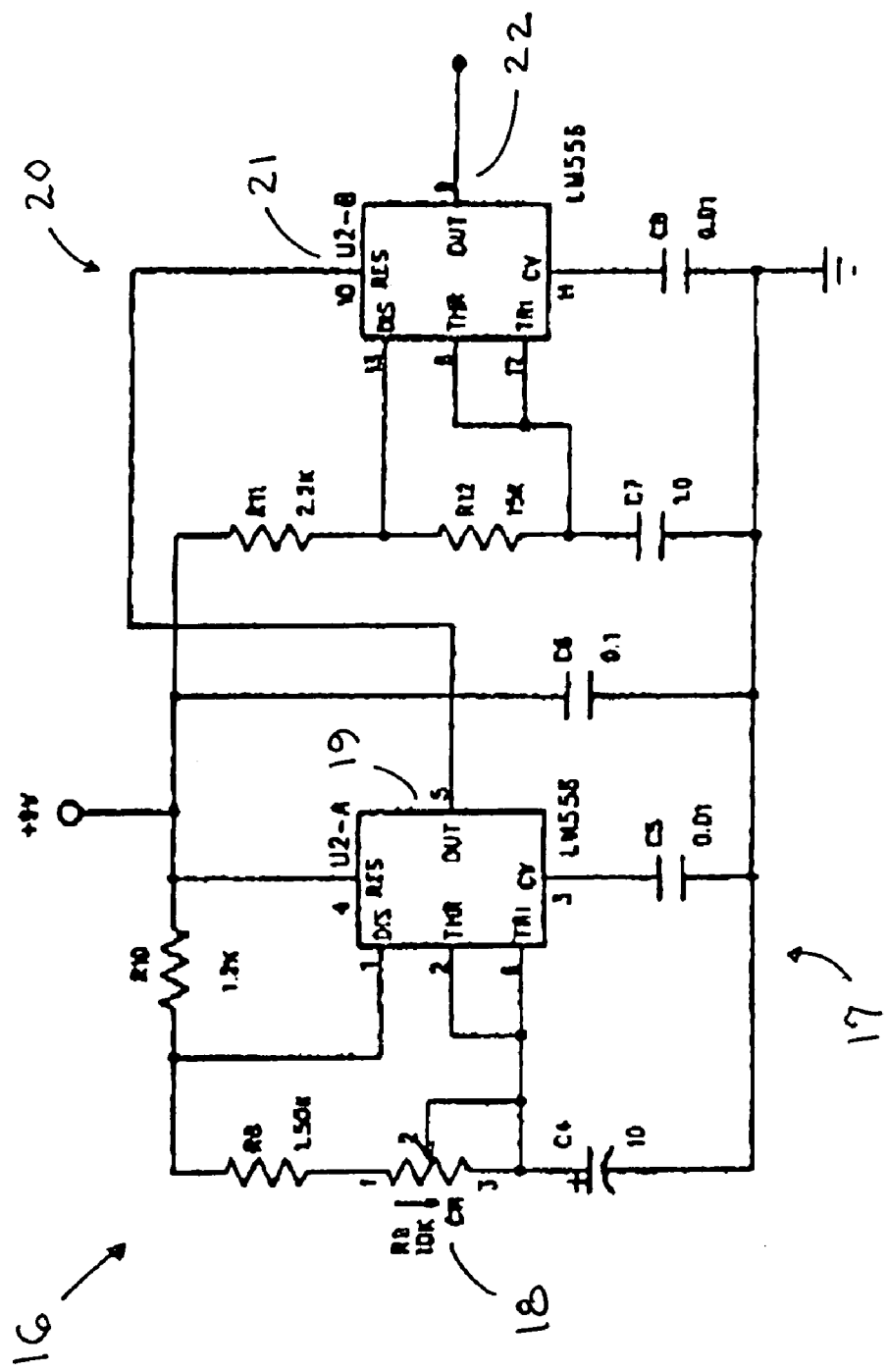
FIG. 3 shows, in a schematic diagram, details of the waveform generation portion of the appetite suppression device of FIG. 1.

As shown in FIG. 3, the signal generating circuit 16 generally comprises a modulation signal generator 17, for generating a signal varying in frequency from approximately four to 40 Hz, and a carrier signal generator 20, for generating a fixed signal of approximately 100 Hz. The modulation signal is superimposed upon the carrier signal with approximately 100% depth of modulation such that the carrier signal is gated on and off by the modulation signal. Although those of ordinary skill in the art will recognize many substantially equivalent implementations, Applicant has found it convenient to implement the modulation signal generator 17 with a 555 timer U2-A configured as an astable multivibrator. The time constants for the 555 timer U2-A are provided by resistor R8, variable resistor R9 and capacitor C4. A frequency control dial 18 is provided on the controller 15 for adjustment of the variable resistor R9 in order that the user may adjust the modulation frequency from approximately four to 40 Hz. In this manner, the user is able to adjust the frequency of the delivered stimulus for maximum comfort level.

Likewise, Applicant has found it convenient to implement the carrier signal generator 20 with a 555 timer U2-B configured also as an astable multivibrator. In this case, however, the time constants are provided by resistor R11, resistor R12 and capacitor C7 in order to produce a fixed 100 Hz signal. As will be apparent to those of ordinary skill in the art, the output 19 from the modulation signal generator 17 is fed to the input 21 of the carrier signal generator 20 in order to superimpose the modulation signal upon the carrier signal. The output 22 from the carrier signal generator 20 thus communicates the modulated signal to the input 43 of the driver and output circuits 32.

Figure 4:
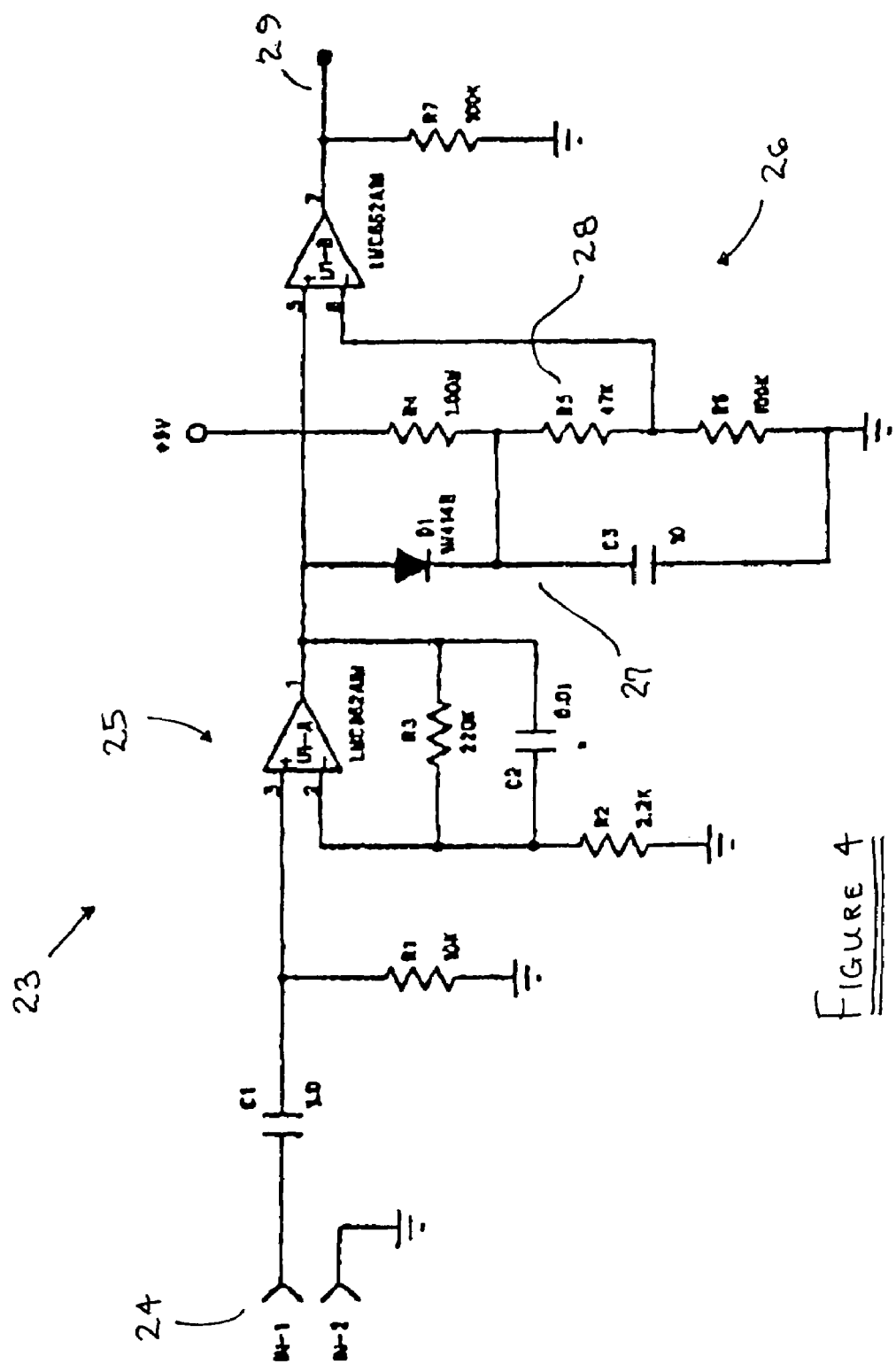
FIG. 4 shows, in a schematic diagram, details of the waveform conditioning portion of the appetite suppression device of FIG. 1.

As shown in FIG. 4, provision may be made for the introduction to the controller 15 of a stimulus signal from an external signal source 30. In this manner, more complex waveforms than described with respect to the signal generating circuit 16 may be utilized to stimulate the tragus area 42 of the user. As will be apparent to those of ordinary skill in the art, such waveforms may be readily generated though any of a variety of devices such as, for example, a personal computer with an audio output port. In any case, if such an additional or alternative implementation is provided, it is desirable that the output signal from the external signal source 30 be conditioned to ensure compatibility with the driver and output circuits 32 of the controller 15. To this end, the signal conditioning circuit 23 generally comprises an amplifier circuit 25 and a variable threshold detection circuit 26. A signal from the external signal source 30 communicated through an input jack 24 to the signal conditioning circuit 23 is thereby first amplified by the amplifier circuit 25, which may comprise a simple implementation of an operation amplifier U1-A. In order to ensure compatibility of the amplified signal with the driver and output circuits 32, however, the variable threshold detection circuit 26 is adapted to further condition the input signal. In particular, a peak detector 27, comprising diode D1 and capacitor C3, and a resistive divider network 28, comprising resistor R4, resistor R5, and resistor R6, are utilized at the inputs to an operational amplifier U1-B to implement a threshold detector automatically operable at between one-third and one-half of the peak voltage level of any input signal.

Figure 5:
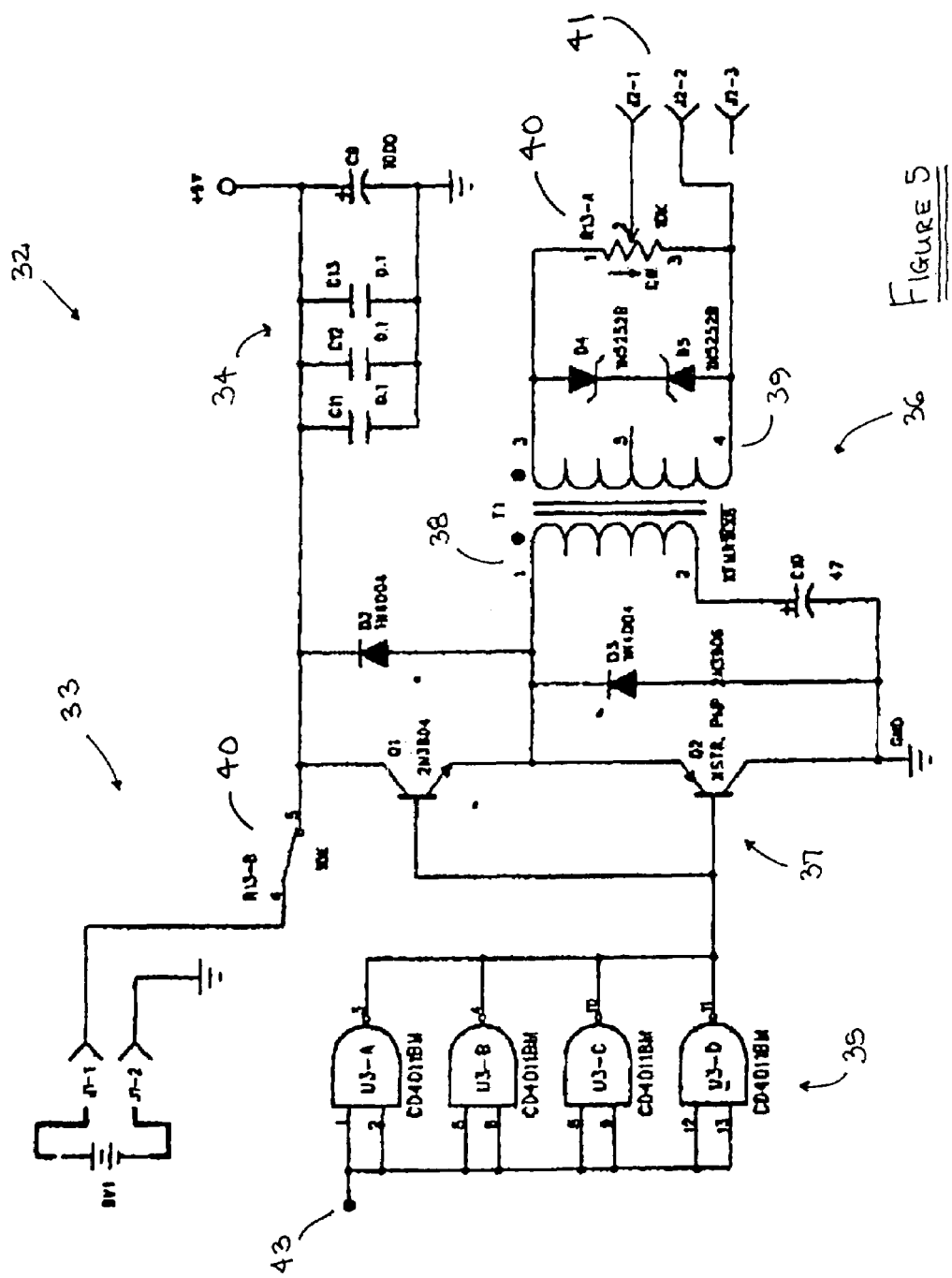
FIG. 5 shows, in a schematic diagram, details of the output portion of the appetite suppression device of FIG. 1.

As shown in FIG. 5, the driver and output circuits 32 generally comprise a power source 33, a current driver 35 and an output circuit 36. As shown in the figure, the power source 33 conveniently comprises a 9-volt alkaline battery 9V1 and a plurality of de-coupling capacitors 34. Although each capacitor C9, C11, C12, C13 shown in the power circuit 33 is utilized as a de-coupling capacitor, it will be better understood further herein that the electrolytic capacitor C9 also supplies transient current to the output circuit 37 of the controller 15, thereby increasing the effective power of the appetite suppression device 10. Finally, an on-off control switch R13-B connected to the on-off level control dial 40 provided on the controller 15 is conventionally utilized to selectively apply battery power to the controller 15.

Regardless of whether an external signal source 30 provides a waveform through the signal conditioning circuit 23 or a waveform is generated by the signal generating circuit 16, the stimulating waveform is first communicated through the input 43 to the driver and output circuits 32 to a CMOS NAND gate array U3 configured as a current driver 35, thereby ensuring adequate driving current for the output network 36.

The output circuit 36 is based upon a complimentary bipolar transistor pair, comprising NPN transistor Q1 and PNP transistor Q2 configured as emitter-followers to implement a current amplifier 37. This current amplifier 37 is utilized to provide the current amplification necessary for driving the primary 38 of a step-up transformer T1. As previously discussed, the electrolytic capacitor C9 in the power source 33 provides the necessary transient current for the current amplifier 37. The secondary 39 of the step-up transformer T1 then produces an output voltage for delivery through an output jack 41 to the electrodes 12 of the headset 11. In order to limit the output voltage to 24 volts, thereby regulating battery life and providing a safety feature for the user, Zener diode D4 and Zener diode D5 are preferably provided across the secondary 39 of the step-up transformer T1. Likewise, diode D2 and diode D3 are provided across the primary 38 of the step-up transformer T1 in order to eliminate back EMF from the primary 38 of the step-up transformer T1, thereby protecting the bipolar transistor pair Q1, Q2.

Although not necessary for the provision of a stimulating signal, it is noted that Applicant has found it desirable to provide a biphasic output as a means of providing a more comfortable stimulation. To this end, an electrolytic capacitor C10 is provided in series with the primary 38 of the step-up transformer T1. As will be apparent to those of ordinary skill in the art, the provision of the electrolytic capacitor C10 provides a biphasic output waveform as current first passes one way, when NPN transistor Q1 is energized, and then the other way, when PNP transistor Q2 is energized.

While the foregoing description is exemplary of the preferred embodiment of the present invention, those of ordinary skill in the relevant arts will recognize the many variations, alterations, modifications, substitutions and the like as are readily possible, especially in light of this description, the accompanying drawings and claims drawn thereto. For example, a variable resistor R13-A may be provided across the secondary 39 of the step-up transformer T1 in order that the user, through adjustment of the on-off-level control dial 40, may control the voltage delivered to his or her tragus region from between zero volts and the limit of 24 volts. In any case, because the scope of the present invention is much broader than any particular embodiment, the foregoing detailed description should not be construed as a limitation of the scope of the present invention, which is limited only by the claims appended hereto.

What is claimed is:

1. An appetite suppression device for providing electro-acupuncture to the tragus regions of a human, said appetite suppression device comprising:
   a controller adapted to produce an electrical signal;
   a plurality of electrodes in electrical communication with said controller, said electrodes being adapted to deliver said signal to the tragus regions of the human; and
   wherein:
      said electrical signal is biphasic;
      said controller comprises a waveform conditioning circuit;
      said signal conditioning circuit comprises a variable threshold detector circuit; and
      said variable threshold detector circuit comprises an operational amplifier circuit having a first and a second input, said second input being in communication with the output from a resistive divider network fed by the output of a peak detector circuit, the input to the peak detector circuit being in communication with said first input to said operational amplifier circuit.

2. The appetite suppression device as recited in claim 1, wherein said electrodes are incorporated into a headset.

3. The appetite suppression device as recited in claim 2, wherein said headset is adjustable in size.

4. The appetite suppression device as recited in claim 1, wherein said waveform conditioning circuit comprises a small signal amplifier.

5. The appetite suppression device as recited in claim 4, wherein said small signal amplifier comprises an operational amplifier circuit.

6. An appetite suppression device for providing electro-acupuncture to the tragus regions of a human, said appetite suppression device comprising;
a controller adapted to produce an electrical signal;
a plurality of electrodes in electrical communication with said controller, said electrodes being adapted to deliver said signal to the tragus regions of the human; and
wherein:
said electrical signal is biphasic;
said controller comprises a waveform generating circuit;
said waveform generating circuit comprises a plurality of astable multivibrators; and
the output of a first astable multivibrator modulates the output of a second astable multivibrator.

7. The appetite suppression device as recited in claim 6, wherein said modulation of the output of said second astable multivibrator by the output of said first astable multivibrator is at a depth greater than 95%.

8. The appetite suppression device as recited in claim 6, wherein the frequency of the output of said first astable multivibrator is variable.

9. The appetite suppression device as recited in claim 8, wherein said frequency of the output of said first astable multivibrator is variable from between approximately four Hertz and approximately 40 Hertz.

10. The appetite suppression device as recited in claim 9, wherein the frequency of the output of said second astable multivibrator is approximately 100 Hertz.

11. The appetite suppression device as recited in claim 6, wherein said electrodes are incorporated into a headset.

12. The appetite suppression device as recited in claim 11, wherein said headset is adjustable in size.

13. The appetite suppression device as recited in claim 6, wherein said controller comprises a waveform conditioning circuit.

14. The appetite suppression device as recited in claim 13, wherein said waveform conditioning circuit comprises a small signal amplifier.

15. The appetite suppression device as recited in claim 14, wherein said small signal amplifier comprises an operational amplifier circuit.

16. The appetite suppression device as recited in claim 13, wherein said signal conditioning circuit comprises a variable threshold detector circuit.

17. The appetite suppression device as recited in claim 13, wherein said controller further comprises a waveform generating circuit.

18. An appetite suppression device for providing electro-acupuncture to the tragus regions of a human, said appetite suppression device comprising:
a controller adapted to produce an electrical signal;
a plurality of electrodes in electrical communication with said controller, said electrodes being adapted to deliver said signal to the tragus regions of the human; and
wherein:
said electrical signal is biphasic;
said controller comprises an output circuit, said output circuit comprising:
a current amplifier; and
a step-up transformer, the output of said current amplifier being in electrical communication with the primary of said step-up transformer; and
the secondary of said step-up transformer is limited in voltage to approximately 24 volts.

19. The appetite suppression device as recited in claim 18, wherein said electrodes are incorporated into a headset.

20. The appetite suppression device as recited in claim 19, wherein said headset is adjustable in size.

21. The appetite suppression device as recited in claim 18, wherein said controller comprises a waveform conditioning circuit.

22. The appetite suppression device as recited in claim 21, wherein said waveform conditioning circuit comprises a small signal amplifier.

23. The appetite suppression device as recited in claim 22, wherein said small signal amplifier comprises an operational amplifier circuit.

24. The appetite suppression device as recited in claim 21, wherein said signal conditioning circuit comprises a variable threshold detector circuit.

25. The appetite suppression device as recited in claim 24, wherein said variable threshold detector circuit comprises an operational amplifier circuit having a first and a second input, said second input being in communication with the output from a resistive divider network fed by the output of a peak detector circuit, the input to the peak detector circuit being in communication with said first input to said operational amplifier circuit.

26. The appetite suppression device as recited in claim 21, wherein said controller further comprises a waveform generating circuit.

27. The appetite suppression device as recited in claim 18, wherein said controller comprises a waveform generating circuit.

28. The appetite suppression device as recited in claim 27, wherein said waveform generating circuit comprises an astable multivibrator.

29. The appetite suppression device as recited in claim 28, wherein said waveform generating circuit comprises a plurality of astable multivibrators.

30. The appetite suppression device as recited in claim 29, wherein the output of a first astable multivibrator modulates the output of a second astable multivibrator.

31. The appetite suppression device as recited in claim 30, wherein said modulation of the output of said second astable multivibrator by the output of said first astable multivibrator is at a depth greater than 95%.

32. The appetite suppression device as recited in claim 30, wherein the frequency of the output of said first astable multivibrator is variable.

33. The appetite suppression device as recited in claim 32, wherein said frequency of the output of said first astable multivibrator is variable from between approximately four Hertz and approximately 40 Hertz.

34. The appetite suppression device as recited in claim 33, wherein the frequency of the output of said second astable multivibrator is approximately 100 Hertz.

* * * * *